US00PP17448P2

(12) United States Plant Patent
Dümmen

(10) Patent No.: US PP17,448 P2
(45) Date of Patent: Feb. 27, 2007

(54) POINSETTIA PLANT NAMED 'DUEARCWI'

(50) Latin Name: *Euphorbia pulcherrima Willd.*
Varietal Denomination: Duearcwi

(75) Inventor: Marga Dümmen, Rheinberg (DE)

(73) Assignee: Dümmer Jungpflanzen GbR, Rheinberg (DE)

( * ) Notice: Subject to any disclaimer, the term of this patent is extended or adjusted under 35 U.S.C. 154(b) by 7 days.

(21) Appl. No.: 11/174,968

(22) Filed: Jul. 5, 2005

(51) Int. Cl.
*A01H 5/00* (2006.01)

(52) U.S. Cl. ..... Plt./304
(58) Field of Classification Search ..... Plt./304
See application file for complete search history.

(56) References Cited

U.S. PATENT DOCUMENTS

PP10,824 P * 3/1999 Zerr ..... Plt./304

OTHER PUBLICATIONS

UPOV ROM GTITM Computer Database, GTI Jouve Retrieval Software 2006/05 Citation for 'Duearcwi'.*

* cited by examiner

*Primary Examiner*—Wendy Haas
(74) *Attorney, Agent, or Firm*—C. A. Whealy

(57) ABSTRACT

A new and distinct cultivar of Poinsettia plant named 'Duearcwi', characterized by its inflorescences with white-colored flower bracts; uniform and rounded plant habit; freely branching habit; early flowering habit; and excellent post-production longevity.

1 Drawing Sheet

Botanical denomination: *Euphorbia pulcherrima* Willd.
Cultivar designation: 'Duearcwi'.

BACKGROUND OF THE INVENTION

The present Invention relates to a new and distinct cultivar of Poinsettia plant, botanically known as *Euphorbia pulcherrima* Willd., and hereinafter referred to by the name 'Duearcwi'.

The new Poinsettia is a product of a planned breeding program conducted by the Inventor in Rheinberg, Germany. The objective of the breeding program is to create new Poinsettia cultivars with uniform plant habit and attractive flower bract coloration.

The new Poinsettia originated from a cross-pollination made by the Inventor in May, 2000 of a proprietary selection of *Euphorbia pulcherrima* Willd. identified as code number 96-0909-003, not patented, as the female, or seed, parent, with a proprietary selection of *Euphorbia pulcherrima* Willd. identified as code number 96-665-001, not patented, as the male, or pollen, parent. The cultivar Duearcwi was discovered and selected by the Inventor as a single flowering plant within the progeny of the stated cross-pollination in a controlled environment in Rheinberg, Germany in December, 2004. The selection of this plant was based on its attractive flower bract coloration.

Asexual reproduction of the new Poinsettia by vegetative terminal cuttings taken at Rheinberg, Germany since December, 2004, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duearcwi'. These characteristics in combination distinguish 'Duearcwi' as a new and distinct cultivar:

1. Inflorescences with white-colored flower bracts.
2. Uniform and rounded plant habit.
3. Freely branching habit.
4. Early flowering habit; response time, about eight weeks.
5. Excellent post-production longevity.

Compared to plants of the female parent selection, plants of the new Poinsettia are more compact and differ in flower bract coloration. Compared to plants of the male parent selection, plants of the new Poinsettia are sturdier and differ in flower bract coloration.

Plants of the new Poinsettia can be compared to plants of the cultivar Fiscor Creme, disclosed in U.S. Plant Pat. No. 10,824. In side-by-side comparisons conducted in Rheinberg, Germany, plants of the new Poinsettia differed from plants of the cultivar Fiscor Creme in the following characteristics:

1. Plants of the new Poinsettia had smaller and lighter green-colored leaves than plants of the cultivar Fiscor Creme.
2. Plants of the new Poinsettia had smaller flower bracts than plants of the cultivar Fiscor Creme.
3. Plants of the new Poinsettia with more flower bracts per inflorescence than plants of the cultivar Fiscor Creme.
4. Flower bracts of plants of the new Poinsettia and the cultivar Fiscor Creme differed in color as plants of the cultivar Fiscor Creme had pale yellow-colored flower bracts.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph differ slightly from the color values cited in the detailed botanical description which accurately describe the colors of the new Poinsettia. The photograph comprises a side perspective view of a single flowering plant of 'Duearcwi' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photograph, following observations and averaged measurements describe plants grown in Rheinberg, Germany during the winter under commercial practice in a glass-covered greenhouse with day and night temperatures about 22° C. and light levels about 4,500 lux. Single plants were grown in 13-cm containers and pinched once about five weeks after planting. Plants were flowered under natural season short day/long night conditions. Plants were about 16 weeks from unrooted cuttings when the photograph and the detailed botanical description were taken.

In the following description, color references are made to The Royal Horticultural Society Colour Chart, 1995 Edition, except where general terms of ordinary dictionary significance are used.

Botanical classification: *Euphorbia pulcherrima* Willd. cultivar Duearcwi.

Parentage:

*Female parent.*—Proprietary selection of *Euphorbia pulcherrima* Willd. identified as code number 96-0909-003, not patented.

*Male parent.*—Proprietary selection of *Euphorbia pulcherrima* Willd. identified as code number 96-665-001, not patented.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About three weeks at 22° C. Winter: About four weeks at 22° C.

*Root description.*—Fibrous, fleshy; white in color.

*Rooting habit.*—Freely branching, dense.

Plant description:

*Plant form.*—Inverted triangle, top of plant rounded.

*Growth habit.*—Upright and uniform plant habit; moderately vigorous.

*Plant height.*—About 20 cm.

*Plant diameter or spread.*—About 35 cm.

*Lateral branch description.*—Quantity per plant: Freely branching habit; about eight lateral branches develop after pinching. Length: About 16.3 cm. Diameter: About 4.5 mm. Internode length: About 1.4 cm. Color: 144B.

*Foliage description.*—Arrangement: Alternate, single. Length: About 7.7 cm. Width: About 4.6 cm. Shape: Ovate. Apex: Apiculate. Base: Obtuse. Margin: Entire with irregular lobing. Venation pattern: Pinnate. Texture, upper and lower surfaces: Glabrous, smooth. Surface: Mostly flat. Color: Developing foliage, upper surface: 137C. Developing foliage, lower surface: 137D. Fully expanded foliage, upper surface: 137B. Fully expanded foliage, lower surface: 137C to 137D. Venation, upper surface: 138B to 138C. Venation, lower surface: 139D. Petiole: Length: About 2.9 cm. Diameter: About 2 mm. Texture, upper and lower surfaces: Glabrous, smooth. Color, upper and lower surfaces: 144B.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Early flowering habit, response time, about eight weeks after start of long nyctoperiod conditions. Post-production longevity: Plants of the new Poinsettia maintain good substance and bract color for about eight weeks under interior conditions and about twelve weeks under greenhouse conditions.

*Quantity of inflorescences per plant.*—One per lateral branch, about eight.

*Inflorescence size.*—Diameter: About 17 cm. Height (depth): About 3 cm.

*Flower bracts.*—Quantity of flower bracts per inflorescence: About 15. Length, largest bracts: About 7.5 cm. Width, largest bracts: About 5.2 cm. Shape: Mostly ovate. Apex: Apiculate. Base: Obtuse. Margin: Entire with irregular lobing. Texture, upper and lower surfaces: Glabrous, velvety. Surface: Smooth. Orientation: Mostly horizontal. Color: Developing bracts, upper and lower surfaces: 145D. Fully developed bracts, upper and lower surfaces: Close to 155C. Venation, upper and lower surfaces: Same as lamina. Flower bract petiole: Length: About 1.3 cm. Diameter: About 1.2 mm. Texture, upper and lower surfaces: Glabrous, smooth. Color, upper and lower surfaces: 144B.

*Cyathia.*—Quantity of cyathia per corymb: About twelve. Diameter of cyathia cluster: About 2.5 cm. Length: About 7.5 mm. Diameter: About 5.5 mm. Shape: Ovoid. Color, immature: 144B. Color, mature: 144A to 144B. Peduncle: Length: About 4 mm. Diameter: About 1 mm. Strength: Moderately strong. Aspect: Curved. Color: 144A. Stamens: Quantity of stamens and staminodes per cyathium: About 30. Anther shape: Oval. Anther length: About 0.5 mm. Anther color: 9B. Amount of pollen: Moderate. Pollen color: 14A. Pistils: Quantity of pistils per cyathium: One. Pistil length: About 8 mm. Style length: About 2 mm. Style color: 144C. Stigma color: 144D. Ovary color: 144B. Nectaries: Quantity of nectaries per cyathium: One. Length: About 4 mm. Color: 1A.

Disease/pest resistance: Resistance to pathogens and pests common to Poinsettias has not been observed on plants grown under commercial conditions.

Temperature tolerance: Plants of the new Poinsettia have been observed to tolerate temperatures from 12° C. to 40° C.

It is claimed:

1. A new and distinct cultivar of Poinsettia plant named 'Duearcwi', as illustrated and described.

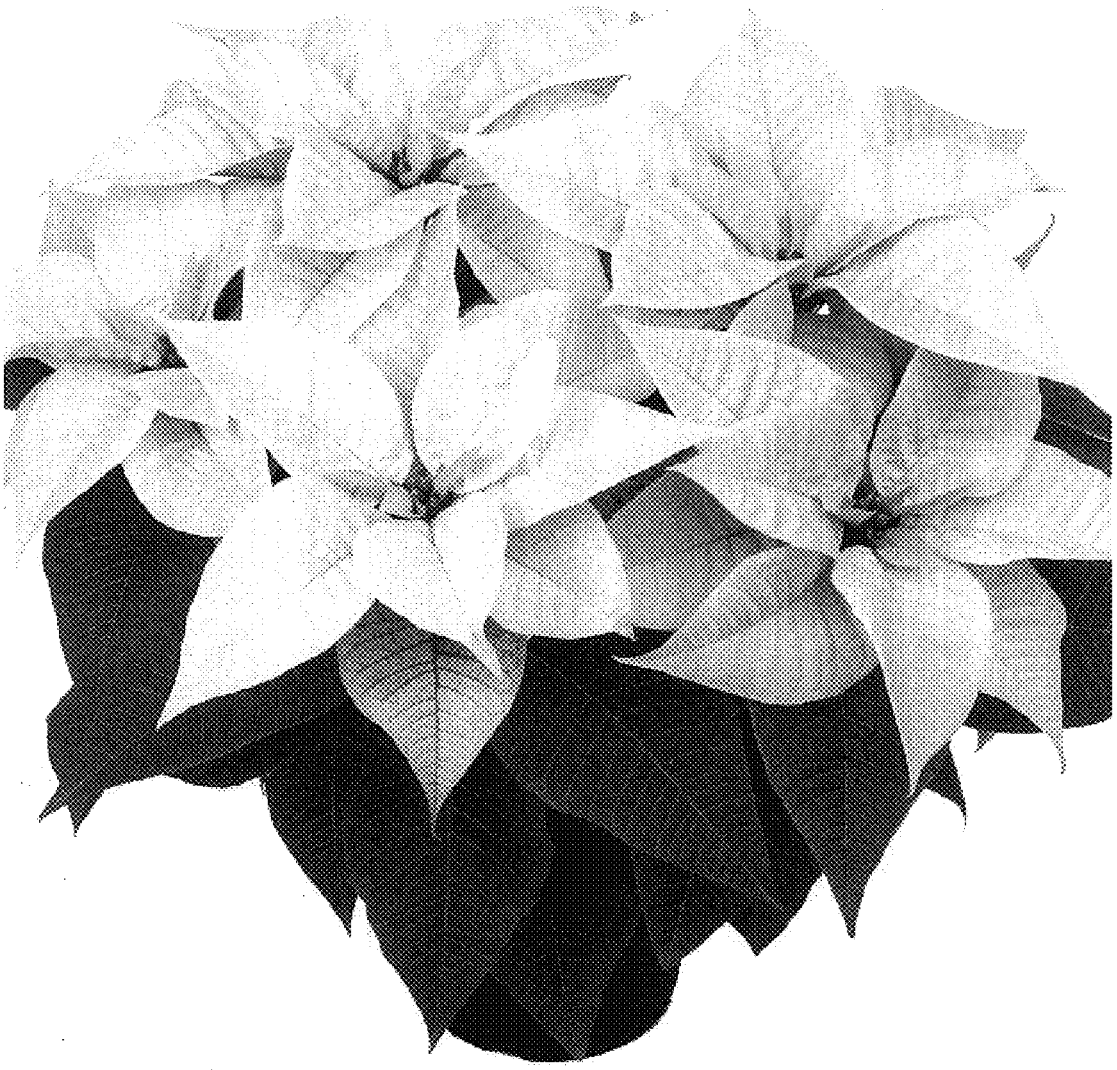

* * * * *